(12) United States Patent
Pagoulatos et al.

(10) Patent No.: US 7,601,121 B2
(45) Date of Patent: Oct. 13, 2009

(54) VOLUME RENDERING QUALITY ADAPTATIONS FOR ULTRASOUND IMAGING

(75) Inventors: Nikolaos Pagoulatos, Athens (GR); Bruce A. McDermott, Bellevue, WA (US); Thomas B. Lindh, Woodinville, WA (US); Roderick C. Gauss, Bellevue, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 672 days.

(21) Appl. No.: 10/889,710

(22) Filed: Jul. 12, 2004

(65) Prior Publication Data

US 2006/0020207 A1    Jan. 26, 2006

(51) Int. Cl.
*A61B 8/00* (2006.01)
(52) U.S. Cl. ...................... 600/443; 382/128
(58) Field of Classification Search ................ 600/443; 382/128; 345/418, 428
See application file for complete search history.

(56) References Cited

U.S. PATENT DOCUMENTS

| | | | |
|---|---|---|---|
| 5,490,512 A | 2/1996 | Kwon et al. | |
| 5,675,554 A * | 10/1997 | Cole et al. | 367/138 |
| 6,447,452 B1 | 9/2002 | Liu et al. | |
| 6,511,426 B1 | 1/2003 | Hossack et al. | |
| 6,542,153 B1 | 4/2003 | Liu et al. | |
| 6,599,245 B1 | 7/2003 | Ma et al. | |
| 2002/0068853 A1 * | 6/2002 | Adler | 600/160 |
| 2005/0049479 A1 * | 3/2005 | Brandl et al. | 600/407 |
| 2009/0009514 A1 | 1/2009 | Pagoulatos et al. | |

OTHER PUBLICATIONS

U.S. Appl. No. 12/211,662 filed Sep. 16, 2008, inventor Nikolaos Pagoulatos, et al.

* cited by examiner

*Primary Examiner*—Brian Casler
*Assistant Examiner*—Jonathan G Cwern

(57) ABSTRACT

Rendering quality parameter values are automatically set or adjusted as a function of acquisition ultrasound parameter values. The rendering quality is automatically selected based on the acquisition quality, such as providing for a higher quality or quality rendering for slower acquisitions. More than two rendering states are provided for a respective, more than two different quality settings.

14 Claims, 4 Drawing Sheets

Figure 4

| Display Layout | Renderer State | | | |
|---|---|---|---|---|
| | Frozen | Stream | Manipulate | Animation |
| 4 quads symmetric | {0.9,2,,True,1} | {0.5,1.0,FALSE,0} | {0.3,0.5,True,120} | {0.8,1.5,True5} |
| 4 quads asymmetric | {0.8,2,,True,1} | {0.4,1.0,FALSE,0} | {0.3,0.5,True,120} | {0.8,1.5,True5} |
| Dual | {0.9,2,,True,1} | {0.5,1.0,FALSE,0} | {0.3,0.5,True,120} | {0.8,1.5,True5} |
| Full Screen | {0.7,2,,True,1} | {0.3,1.0,FALSE,0} | {0.3,0.5,True,120} | {0.5,1.5,True5} |

VOLUME RENDERING QUALITY ADAPTATIONS FOR ULTRASOUND IMAGING

BACKGROUND

The present invention relates to quality adaptations in volume rendering for ultrasound imaging.

The quality of a three dimensional representation or volume rendered image by an ultrasound system is dependent on the acquisition quality as well as the rendering quality. Acquisition quality is determined by the ultrasound data acquisition systems, such as the beamformer's azimuthal beam density, elevational beam density (or frame density) and range sampling density of the echo data in a three dimensional space or volume. The azimuthal beam density and frame density can also be determined by an apparatus different and separate from the beamformer. This apparatus can directly control the azimuthal beam density (or frame density) of the ultrasound acquisition. The acquisition quality is dependent on the transducer, beamforming and backend signal processing parts of an ultrasound system. The acquisition quality trades off higher image quality with acquisition volume rate or speed. Higher sampling density is achieved by acquiring additional samples per beam, additional beams per frame, and additional frames per volume. Increasing the sampling density may result in a lower volume acquisition rate.

The rendering quality is determined by the density used to sample the acquisition space for volume rendering. The samples acquired by the ultrasound system are re-sampled to a rendering grid for volume rendering. Rendering quality is related to the volume rendering algorithm. Rendering quality trades off a higher quality rendered image with rendering rate or speed given fixed hardware rendering resources.

The settings used by an ultrasound system for the acquisition and rendering are independently set. Manual controls, such as knobs or dials, allow a user to select acquisition related parameters and associated quality. Separate or different knobs or dials allow a user to select rendering quality and associated parameters. Where a user manually changes parameters, such as associated with a slower acquisition rate, the rendering parameters may be maintained at the same values, resulting in a lower rendering resolution than is possible given the extra time available for rendering.

In volume rendering algorithms, higher quality rendering is more computationally intensive and therefore slower. Volume rendering algorithms use different parameters that determine the quality of the rendered image. The rendering quality parameters trade-off image quality with system performance. System performance may be indicated by rendering speed and/or system response time to user interaction. For example, two different states of volume rendering are provided. One state operates with streaming volumes. A plurality of different representations is sequentially generated as data is acquired and provided to the rendering algorithm. Another state is a manipulation state. The user interacts with the volume image, such as to perform a trace operation, adjust brightness, adjust opacity, rotate viewing angle or perform another manipulation or editing option. Different rendering qualities and associated resolutions are provided for the two different states. For example, streaming volumes are rendered. The user then manipulates or changes state for editing. As a result of the change in state, the rendering algorithm parameters are altered to provide a lower quality or lower resolution image in order to provide faster response time to user interactions and manipulations. To change the quality, the rendering sampling density in all three dimensions is altered.

BRIEF SUMMARY

By way of introduction, the preferred embodiments described below include methods and systems for adapting rendering quality for ultrasound imaging of a volume. In one embodiment, rendering resolution parameter values are automatically set or adjusted as a function of acquisition ultrasound parameter values. The rendering quality is automatically selected based on the acquisition quality, such as providing for a higher quality or resolution rendering for slower acquisitions. In another embodiment, more than two rendering states are provided for a respective, more than two different resolution settings. For example, different resolution settings are provided for streaming, manipulation, frozen and animation states. Since the frozen state is less limited by processing time, the frozen state may be rendered with a highest quality or resolution. In yet another embodiment, the rendering is provided with two different sampling density variables, such as an in-plane or XY sampling density and a viewing direction or z sampling density. The separation may allow for a more versatile trade-off between image quality and performance. In yet another embodiment, a Boolean flag indicates whether an adaptive sampling algorithm is to be used, and/or a threshold controls the in-plane adaptive sampling algorithm. In this in-plane adaptive sampling algorithm, fewer than all the pixels or in-plane spatial locations are used for rendering along the viewing direction. Where little difference is provided between two or more rendered pixels, a pixel or pixels in between may be interpolated rather than rendered. The Boolean flag indicates whether the adaptive interpolation is to be used. The threshold indicates the amount of difference between pixel values that is acceptable to avoid rendering and provide interpolation. Furthermore in another embodiment, additional flags for various image processing algorithms (that enhance image quality at the expense of speed) can be included in the rendering quality parameter set. Each of the embodiments summarized above may be used independently or in combination.

In a first aspect, a method is provided for adapting rendering quality for ultrasound imaging of a volume. At least one ultrasound acquisition parameter value is set. The volume is scanned as a function of the ultrasound acquisition parameter value. A processor sets at least one rendering resolution parameter value as a function of the ultrasound acquisition parameter value. An ultrasound image is rendered from data acquired by the scan. The rendering is performed as a function of the rendering resolution parameter value.

In a second aspect, a system is provided for adapting rendering quality for ultrasound imaging of a volume. A beamformer system is operable to scan the volume as a function of at least one ultrasound acquisition parameter value. The value is selected for one of azimuthal beam spacing, elevational beam spacing, frame spacing, depth, imaging frequency, parallel beam processing, imaging depth, 2D field-of-view (FOV), 3D FOV and combinations thereof. A three dimensional rendering processor is operable to render an ultrasound image representing the volume from data acquired by the beamformer as a function of the ultrasound acquisition parameter value. The rendering is a function of at least one rendering resolution parameter value. The rendering resolution parameter value is set as a function of the ultrasound acquisition parameter value. The rendering resolution parameter value is set for one of in-plane sampling density, viewing direction sampling density, flag for the in-plane adaptive sampling, adaptive sampling threshold, interpolation density and combinations thereof.

In a third aspect, a method is provided for adapting rendering quality for ultrasound imaging of a volume. Three or more different renderings states are provided for user selection. Each of three or more different rendering states corresponds to a respective different resolution setting. A three-dimensional representation of the volume is rendered in one of the three different rendering states.

In a fourth aspect, a method is provided for adapting rendering quality for ultrasound imaging of a volume. An in-plane sampling density is set as a separate variable than a viewing direction sampling density. A three-dimensional ultrasound representation is rendered as a function of the in-plane sampling density and the viewing direction sampling density.

In a fifth aspect, a method is provided for adapting rendering quality for ultrasound imaging of a volume. One of a Boolean flag for interpolation, a threshold for interpolation or combinations thereof is set. The Boolean flag indicates whether any interpolation occurs, and the threshold indicates when possible interpolation is to be performed. A three-dimensional ultrasound representation is rendered as a function of the Boolean flag, the threshold or the combination thereof.

In a sixth aspect, a method is provided for changing two or more rendering quality parameters as a result of changing the display layout. By changing two or more rendering quality parameters based on the active display layout, a more optimal trade-off between rendering image quality and speed can be found.

The present invention is defined by the following claims, and nothing in this section should be taken as a limitation on those claims. Further aspects and advantages of the invention are discussed below in conjunction with the preferred embodiments and maybe later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Different embodiments are described below for use individually or in combination. In general, the embodiments are described in two groupings. The first grouping is of embodiments where rendering quality is based on acquisition quality. Acquisition parameter values are used to determine rendering resolution values, more likely providing optimum quality and performance through automated consideration of both the acquisition and rendering settings. A second group of embodiments may be independent of acquisition parameters. Rendering resolution parameter values are automatically determined based on the state of the rendering system and the display layout used. For example, four rendering states are provided, such as streaming, manipulation, frozen and animation rendering states. Based on the rendering state and the display layout (e.g. full screen, dual image, quad image or other screen divisions for multiple images), the appropriate rendering resolution parameter values are selected. The different rendering resolution parameters include in-plane resolution of the image, the resolution of the image along the viewing orientation, and any adaptive optimization, such as interpolation. Rendering is optimized, such as providing for a greatest resolution in rendering for frozen images an even lesser resolution for streaming images and a least resolution for manipulation images. In the case where the system is in the animation rendering state (repetitive sequence of rendered images based on the same volume data), the quality of rendering is determined based on a number of parameters including but not limited to speed of animation, smoothness of animation, and choice of rendering mode. Rendering states with the most processing time are optimized to provide the maximum amount of quality or resolution.

Figure 1:
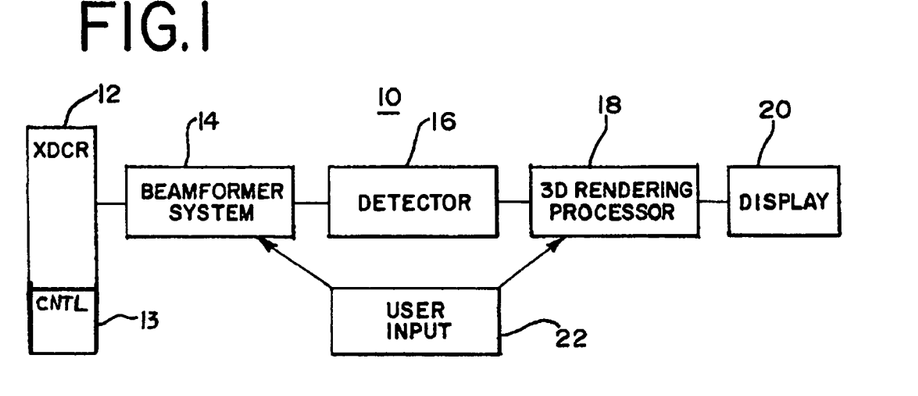
FIG. 1 is a block diagram of one embodiment of an ultrasound system for adapting rendering quality.

FIG. 1 shows one embodiment of a system 10 for adapting rendering quality for ultrasound imaging of the volume. The system 10 includes a transducer 12, a controller 13, a beamformer 14, a detector 16, a 3D rendering processor 18, a display 20 and a user input 22. Additional, different or fewer components may be provided, such as providing the 3D rendering processor 18 and the display 20 without other components. In another example, a memory is provided for storing data externally to any of the components of the system 10. The system 10 is an ultrasound imaging system, such as a cart based, permanent, portable, handheld or other ultrasound diagnostic imaging system for medical uses, but other imaging systems may be used.

The transducer 12 is a multidimensional transducer array, one-dimensional transducer array, mechanically swept transducer also known as wobbler transducer or other transducer operable to scan mechanically and/or electronically in a volume. For example, a wobbler transducer array is operable to scan a plurality of planes spaced in different positions within a volume. As another example, a one-dimensional array is rotated within a plane along the face of the transducer array or an axis spaced away from the transducer array for scanning a plurality of planes within a volume. As yet another example, a multidimensional transducer array electronically scans along scan lines positioned at different locations within a volume. The scan is of any formats, such as sector scan along a plurality of frames in two dimensions and a linear or sector scan along a third dimension. Linear or vector scans may alternatively be used in any of the various dimensions.

The beamformer system 14 is a transmit beamformer, a receive beamformer, a controller for a wobbler array (e.g., the controller 13 that is separate from or part of the beamformer system 14, filters, combinations thereof or other now known or later developed components for using and setting ultrasound acquisition parameters. The beamformer system 14 is operable to generate waveforms and receive electrical echo signals for scanning the volume as a function of ultrasound acquisition parameter values. The beamformer system 14 controls the beam spacing both in azimuth and elevation directions. The distribution of beams within a plane or within the volume is controlled by the beamformer by focusing, such as through apodization and relative delays. Another ultrasound acquisition parameter is frame spacing. The frame spacing provides for the different positions of two-dimensional scans within the volume. For example, a wobbler transducer displaces a one-dimensional array to cause different planes within the volume to be scanned electronically in two-dimensions. Another ultrasound acquisition parameter is the beam sampling density. The beam sampling density controls the number of samples along any given acoustic beam. Another ultrasound acquisition parameter is the depth. The depth or distance away from the transducer 12 for which ultrasound data is received and used for imaging may be shallow or deep depending on the application. Yet another ultrasound acquisition parameter is the imaging frequency. An imaging frequency includes the transmit frequency, a receive frequency or combinations thereof. Waveforms are generated within a frequency band having a center frequency or imaging frequency for transmission. Typical ultrasound frequencies are from 1 to 12 megahertz, but other frequencies may be used. The receive frequency is the same as the transmitted frequency, but may be a harmonic of the transmit frequency. Yet another ultrasound acquisition parameter is parallel beam processing. Parallel beam processing provides for the transmission and/or reception of multiple beams in a single transmit event. For example, a wide beam is transmitted, and a plurality of spatially distinct receive beams are formed in response to the single transmission. Parallel processing is provided by the receive beamforming operations to form the two distinctive receive beams. More than two beams may be used or generated for parallel beam processing. No parallel beam processing may also be used.

The beamformer system 14 uses all or a subset of values of the ultrasound acquisition parameters for scanning a volume. The value may be associated with an integer or real number, such as a depth, frame spacing, azimuthal beam spacing, elevational beam spacing or imaging frequency. A value may be associated with a selection of a particular process, such as no parallel beam processing, some receive parallel beam processing, the number of beams used for parallel beam processing or other variable for parallel beam processing. For example, U.S. Pat. No. 5,675,554, the disclosure of which is incorporated herein by reference, discloses various parallel beam formation parameters. The beamformer system 14 is configured to operate pursuant to the selected values for the various parameters. The scans are then performed as a function of the values, such as values for azimuthal beam spacing, elevational beam spacing, frame spacing, depth and imaging frequency. The selected values are part of the determination of the volume acquisition rate. The acquisition rate is a speed with which the desired volume is scanned. Given a depth, azimuthal extent and elevational extent of a volume and other acquisition parameters, the volume is scanned once within a particular time period.

The detector 16 is a B-mode detector, Doppler detector, video filter, temporal filter, spatial filter, processor, image processor, combinations thereof or other now known or later developed components for generating image information from the acquired ultrasound data output by the beamformer system 14. In one embodiment, the detector 16 includes a scan converter for scan converting two-dimensional scans within a volume associated with frames of data to two-dimensional image representations. In other embodiments, the data is provided for representing the volume without scan conversion.

The three-dimensional rendering processor 18 is a general processor, a data signal processor, graphics card, graphics chip, personal computer, motherboard, memories, buffers, scan converters, filters, interpolators, field programmable gate array, application specific integrated circuit, analog circuits, digital circuits, combinations thereof or any other now known or later developed device for generating three-dimensional representations from input data in any one or more of various formats. The three-dimensional rendering processor 18 includes software or hardware for rendering a three-dimensional representation, such as through alpha blending, minimum intensity projection, maximum intensity projection, surface rendering, or other now known or later developed rendering technique.

The three-dimensional rendering processor 18 is operable to render an ultrasound image representing the volume from data acquired by the beamformer system 14. The rendering is performed as a function of a value for one or more rendering quality parameters. A rendering quality parameter is a variable operable to affect the quality and/or resolution of the rendered image. For example, rendering quality parameters include an in-plane sampling density, a viewing direction sampling density, flag for the in-plane adaptive sampling, adaptive sampling threshold, an interpolation density, combinations thereof or other parameters. For intensity projection based rendering, each pixel within a two-dimensional plane is associated with a ray line or viewing direction through the volume. The number of pixels sampled within the plane is the in-plane sampling density. The number of data points sampled or used along each viewing direction for each pixel is the viewing direction sampling density. The interpolation density provides a number of pixels associated with interpolated values from adjacently rendered pixels as an alternative to individually rendering each and every pixel. For example, every other in-plane pixel is provided as a candidate for interpolation. The adjacent pixels along one- or two-dimensions are rendered. The resulting rendered pixels are examined. If the resulting pixels are within a threshold difference, then the value for the pixel in between is interpolated rather than rendered, reducing the numbers of calculations performed for generating a three-dimensional representation. Whether interpolation is performed at all is encoded in a Boolean flag used for the in-plane adaptive sampling method. The interpolation spacing, such as every other or every third pixel, may be another interpolation density parameter. Yet another interpolation density parameter may be the threshold to determine whether interpolation as opposed to rendering is performed for any given pixel. Other adaptive or non-adaptive interpolation functions may be used.

One or more rendering quality parameter values are set as a function of one or more of the ultrasound acquisition parameter values. For example, values for the in-plane sampling density and the viewing direction sampling density are set as a function of four or more or all of the ultrasound acquisition parameter values. In one embodiment, specific acquisition parameters are tied to specific rendering quality parameters. In other embodiments, the ultrasound acquisition parameter values determine an acquisition speed. The rendering quality parameter values are then selected in any of various combinations to provide a rendering speed that substantially matches the acquisition speed.

The selection or setting of the rendering quality parameter values is performed automatically by the three-dimensional rendering processor 18 or another processor without further user input. In alternative embodiments, additional user input may be used to set one or fewer than all of the rendering quality parameter values. In yet other alternative embodiments, the user separately sets all of the rendering quality parameter values.

The display 20 is a monitor, CRT, LCD, plasma screen, flat panel, projector or other now known or later developed display device. The display 20 is operable to generate a rendered three-dimensional representation. For example, a two-dimensional image representing a three-dimensional volume through rendering is displayed. As discussed below, the three-dimensional rendering processor 18 in combination with the display 20 may generate images in any of various rendering states.

The user input 22 is a keyboard, touch screen, mouse, trackball, touchpad, dials, knobs, sliders, buttons, combinations thereof or other now known or later developed user input devices. In one embodiment, the user input 22 includes a knob, dial or slider specifically labeled for different quality levels of three-dimensional representations. The labeling may be provided by software display or permanent lettering. The user input 22 connects with the beamformer system 14 and the three-dimensional rendering processor 18. The user input 22, such as a single knob or dial or slider labeled as discussed above, is operable for indicating a range of image qualities. For example, a range of 3 or 6 different image qualities from low to high is provided. The range may be application specific, such as providing three levels for OB and 6 levels for fetal echocardiograms. Each of the quality levels for a given application is associated with a set of variables. The set of variables correspond to ultrasound acquisition parameter values and rendering quality parameter values. The values within a set are determined based on the system capabilities and the desired volume rate or overall speed provided by acquisition and rendering. For example, a high quality or high resolution image is provided by settings for low volume rate, resulting in higher overall rendered image quality. Higher quality is provided by a more thorough scan for acquiring data. Since a lower scan rate is provided, the three-dimensional rendering processor 18 is automatically configured to make use of the additional time. The configurations provide for greater rendering quality, such as through changes in sampling densities, amounts of interpolation, or other settings. Any of the various rendering quality parameter values are set based on interactions with other values and associated imaging results. Since the in-plane and viewing direction densities may be separately set, more optimum or full range of options are available. Viewing direction density is set to avoid image artifacts, but at a different level than the in-plane sampling density set to avoid a blocky appearance. For low quality imaging, the in-plane sampling density may be set to 0.6 and the viewing direction density set 0.7 for OB applications or 0.4 and 0.5 for fetal echo applications. For high quality, the settings may be 0.9 and 1 for OB and 0.7 and 0.8 for fetal echo. The settings above are merely examples, and may include other values, parameters, applications or combinations of values.

In one embodiment, the user control 22 is used during real time imaging, such as streaming volumes, for adjusting the quality levels. In other embodiments, the quality level is preset based on the chosen imaging application (e.g., OB, GYN, fetal echo and others) or adjusted prior to generating images from a memory or during acquisition. In yet another embodiment, the user sets various ultrasound acquisition parameters using multiple input devices. The rendering quality parameters are then set automatically as a function of the acquisition parameter values. Setting rendering quality parameter values as a function of the settings for ultrasound acquisition parameter values includes the selection of sets of values for both acquisition and rendering parameters. The rendering values are selected as a function of the acquisition values for inclusion with a same set and use at a same time.

Using a single control for both acquisition and rendering quality adjustments, a more optimum tradeoff between performance and image quality given the capabilities of a system 10 may be selected. Optimization is additionally provided where acquisition parameters are manually set, and rendering quality parameters are then determined in real time as a function of the acquisition parameters. In either case, the user interaction to obtain more optimal volume rendering is simplified. By increasing the rendering quality during slower acquisition, the processing power of the three-dimensional rendering processor 18 is used to improve the quality of the rendered image without dropping rendering of any acquired volumes. During high speed operation with lower quality volume acquisitions, the quality of the rendered image may be reduced so that the 3D rendering processor 18 has a similar or matched speed with the incoming volume data. Any of various differences in rates between different settings may be provided, such as providing from 2-8, 8-16 or other range of volumes per second in both acquisition and rendering speed.

Figure 2:
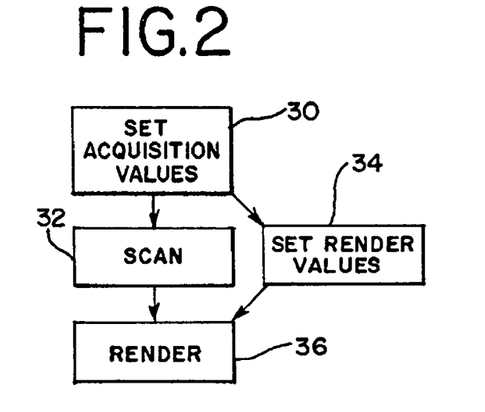
FIG. 2 is a flow chart diagram of one embodiment of a method for adapting rendering quality for ultrasound imaging of a volume.

FIG. 2 shows one embodiment of a method for adaptive rendering quality for ultrasound imaging of a volume. Additional, different or fewer acts may be performed in the same or different order than shown in FIG. 2. The method is implemented using the system of FIG. 1 or a different system. The method matches rendering quality to acquisition quality.

In act 30, ultrasound acquisition parameter values are set. The value for one, all or a subset of the parameters of azimuthal beam spacing, elevational beam spacing, frame spacing, depth, an imaging frequency, beam sampling density, parallel beam processing, scan extent and combinations thereof are selected. For example, a user sets a beam spacing, a depth and an imaging frequency. The processor then sets a frame spacing based on the wobbler speed.

The values of the different parameters are set in response to user input. For example, the user selects specific values for each parameter. As another example, the user selects an imaging application. Given a sensed type of transducer in the selected application, the system automatically selects values for the various parameters. Combinations of user specific selection and system set different parameters based on the user selections may be used. Groups of settings are provided for selection by the user in other embodiments. In yet another embodiment, the user merely selects a quality of imaging and stored settings are selected based on the quality and any other factors, such as the selected imaging application or examination preset.

An acquisition speed results from the settings of the various ultrasound acquisition parameter values. In one embodiment, the user specifically selects a speed and values are set based on the selected speed. Alternatively, the values are set, resulting in setting of the acquisition speed. The acquisition speed corresponds to an amount of time during which ultrasound energy is used to scan an entire volume. The size, shape, sampling density and other factors may affect the acquisition time.

In act 32, the volume is scanned as a function of the ultrasound acquisition parameter values. The volume may be scanned once or repetitively using the same or different parameter values. The scan is performed as a function of the values.

In act 34, at least one rendering quality parameter value is set with a processor. The rendering quality parameter value is set as a function of one or more ultrasound acquisition parameter values. For example, the rendering quality parameter value is automatically set based on an ultrasound acquisition parameter value without additional user input. The rendering quality parameter value is selected with a group of settings that include the ultrasound acquisition parameter values, or is calculated or looked up from a memory once an ultrasound acquisition parameter value or values are determined. Accordingly, acts 30 and 34 may occur at a same time or sequentially.

Any of various rendering quality parameters may be set, such as in-plane sampling density, viewing direction sampling density, an interpolation density, an interpolation threshold, an interpolation flag and combinations thereof. Any of various calculations may be used for determining a value for a given parameter based on one or more values of an acquisition parameter. In one embodiment, sets of parameters are examined through experimentation to provide a substantial match of the rendering speed to the acquisition speed while providing the most optimal rendering for a given application and imaging system. Any relationship of specific acquisition parameters to specific rendering parameters or groups thereof may be used. By automatically setting the rendering quality parameters with a processor, the system performance may be optimized with minimal additional user input.

In act 36, an ultrasound image is rendered from the data acquired in act 32. The rendering is performed as a function of the rendering quality parameter values. A three-dimensional representation is rendered onto a two-dimensional display using the rendering quality parameter values. The rendering quality parameter values affect the speed with which the rendering occurs. Where more rendering time is available due to a slower acquisition speed, rendering quality parameter values providing a higher resolution or overall quality image may be provided.

Figure 5:
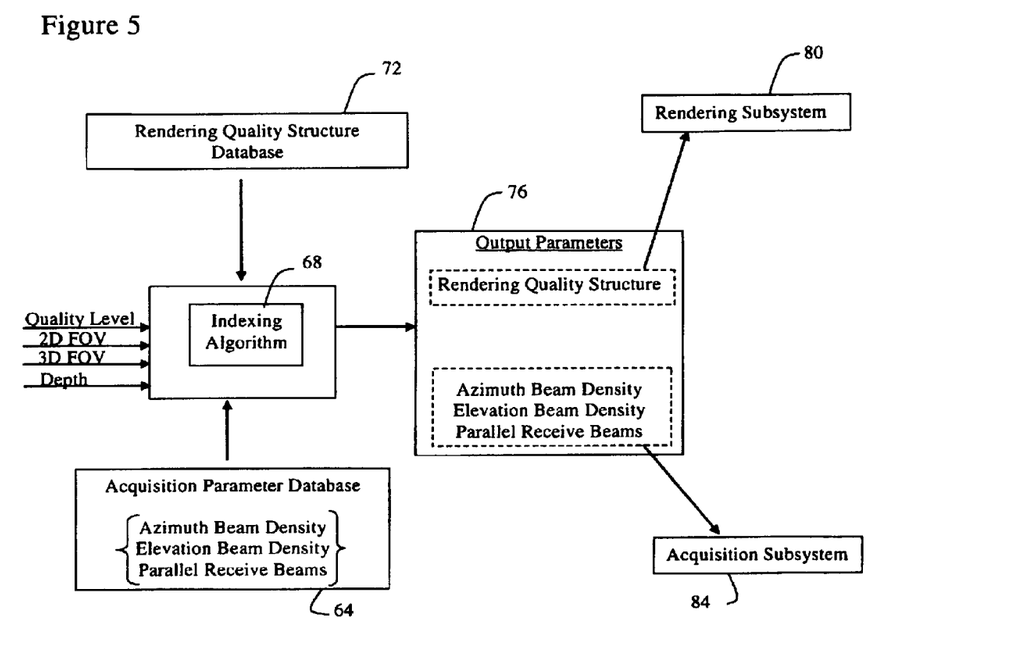
FIG. 5 is a flow chart diagram of one embodiment of software used for implementing the method of FIG. 2.

In one embodiment, the user or processor sets the various acquisition parameter values based on any number of inputs. In an alternative embodiment, the acquisition parameter values are set with a single control as represented in FIG. 5. The single quality control is operable to select the different ultrasound acquisition parameter values from a range of settings. For example, acquisition is controlled with a single quality control indicating a range of image qualities. The ultrasound acquisition parameter values associated with a particular quality and application are selected, such as via an acquisition parameter database 64 and an indexing algorithm 68, using the single control. The rendering quality parameter values are also selected, such as via a rendering quality structure database 72 and the indexing algorithm 68, using the single control. The rendering quality parameter values are selected to correspond to the indicated image quality. The rendering quality parameter values are set free of additional user input in addition to controlling acquisition with a single control. The sets of acquisition and rendering parameter values associated with a given quality setting are formed based on matching the acquisition speed to the rendering speed. As a result, the rendering quality parameter values are set as a function of the acquisition parameter values. Output parameter values 76 are sent to a rendering subsystem 80 and an acquisition subsystem 84, respectively.

Figure 3:
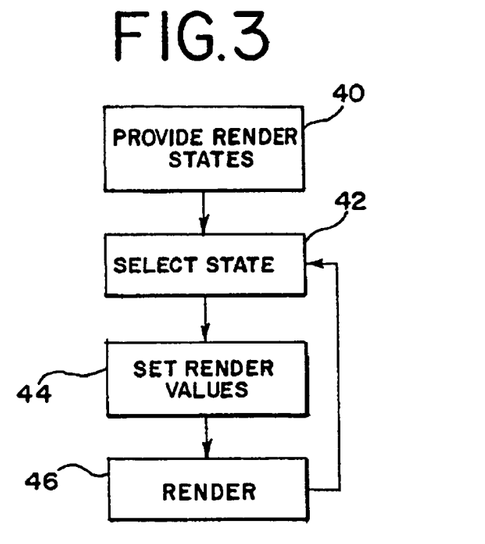
FIG. 3 is a flow chart of another embodiment of a method for adapting rendering quality for ultrasound imaging of a volume.

FIG. 3 shows one embodiment of a method for adapting rendering quality for ultrasound imaging of a volume. Additional, different or fewer acts in the same or different order shown in FIG. 3 may be used. The method of FIG. 3 is implemented using the system of FIG. 1 or different systems. For example, the method of FIG. 3 is implemented on a computer, work station or other three-dimensional rendering processor separate from an acquisition system. The ultrasound data used for rendering are stored or provided from any of various possible sources. As another example, the method of FIG. 3 is implemented on an ultrasound medical diagnostic ultrasound imaging system that includes a beamformer system. The method provides rendering with or without consideration of acquisition values or speed.

In act 40, three or more different rendering states are provided for user selection. Interface software for operation with the three-dimensional rendering makes various functions available to the user, including rendering states. For example, a frozen state, a streaming state, a manipulation state and an animation state are provided. Different, fewer or additional states may be provided. The frozen state is associated with a statically displayed ultrasound image of a three-dimensional representation.

The streaming state corresponds to a non-repeating sequence of ultrasound images, which are generated from the same volume data. For example, ultrasound scans of a volume are performed in real time and resulting three-dimensional representations are also generated in real time with the scans. As another example, data stored in a memory is output in sequence for rendering. The rendering is repetitively performed for different sets of data representing the same volume from a non-repeating sequence of ultrasound data.

In the manipulation state, one or more ultrasound images are displayed in response to a change in a rendering parameter. For example, a user adjusts brightness, opacity, a viewing direction, an amount of shading, a rendering quality parameter value, or performs other manipulation or editing of the imaging. The rendering parameter may be changed during a streaming state, transitioning the software to the manipulation state. Alternatively, the manipulation state is entered from a frozen state.

The animation state corresponds to a repeating sequence of ultrasound images. For example, a sequence of images is selected for repetitive viewing in an endless loop. As another example, a single set of data representing a volume is viewed repetitively from different viewing angles, such is associated with rotating the viewing direction over any range of angles (e.g. 30 to 60 degrees). Any of various axes individually or in combination may be used for rotation and any rotation speed may be provided. Another example of animation may be a same viewing direction of a same volume but with repetitive changes in opacity, brightness or other parameter. The rendering for an animated state may be performed in real time for each repetition of an image or may be performed once and stored for repetitive output. By performing real time rendering even in an animated state, editing or transition to the manipulation state may be more efficiently performed.

Each of the different rendering states corresponds to respective different resolution or quality settings. For example, a frozen state has the highest quality as compared to streaming and manipulation states. Since the rendering processor is not needed for continuous or ongoing rendering, additional processing time may be used to generate a frozen image at the highest quality. The statically displayed ultrasound image has a higher quality than ultrasound images of either a repeating or non-repeating sequences in one embodiment. When the rendered images of a repeating sequence are stored, the repeating sequence may have similar or higher quality than the frozen state. The ultrasound images of the repeating sequence may have a higher quality than of the non-repeating sequence since information about the repeating images may assist in later rendering of the same image or because the repeating sequence is rendered over a longer period of time for repetitive viewing. Ultrasound images of the non-repeating sequence (i.e. streaming state) may have a higher quality than one or more ultrasound images displayed in response to a change in a rendering parameter (i.e., manipulation state). Due to a change in the rendering parameter, the rendering may be slowed, resulting in a lower quality.

For example, a user is viewing ultrasound images in a frozen or streaming state. Once a manipulation occurs, the rendering processor reduces quality while processing the change. By providing different qualities for the different states, the quality may be optimized to the available processing power for rendering. Each of the different states may have a different quality than the other rendering states. Other relative quality levels for the different states may be provided.

The differences in quality result from different rendering and performance settings. The settings are provided as a function of the different rendering states. For example, each rendering state is associated with different combinations of values for one, two or more of various parameters. The parameters include in-plane sampling density, viewing direction sampling density, an interpolation density, a Boolean flag for interpolation, an interpolation threshold, a number of simultaneously displayed images or combinations thereof. A same parameter in different rendering states may have a same setting. At least one parameter value is different in one rendering state than in another rendering state, resulting in a different quality.

The number of simultaneously displayed images corresponds to a full screen, dual image, quad image or other displays of one or multiple images in a same display or screen. The display layout in addition to the state may result in different settings for quality. For example, the more sections provided in a display from displaying different images may result in lesser quality or quality in rendering each of the images. The number of rays cast through a volume for sampling on a viewing direction may be the same or different depending on the number of sections or images simultaneously displayed. For example, an image is displayed in a 200×200 pixel window for a quad display and a 400×400 pixel window for a full display. By providing an in-plane sampling density of 0.5, rays are cast along 100×100 grouping of pixels or every other pixel and the remaining pixels are interpolated. For a full image, a sampling may be increased to avoid the reduction in quality.

Figure 4:
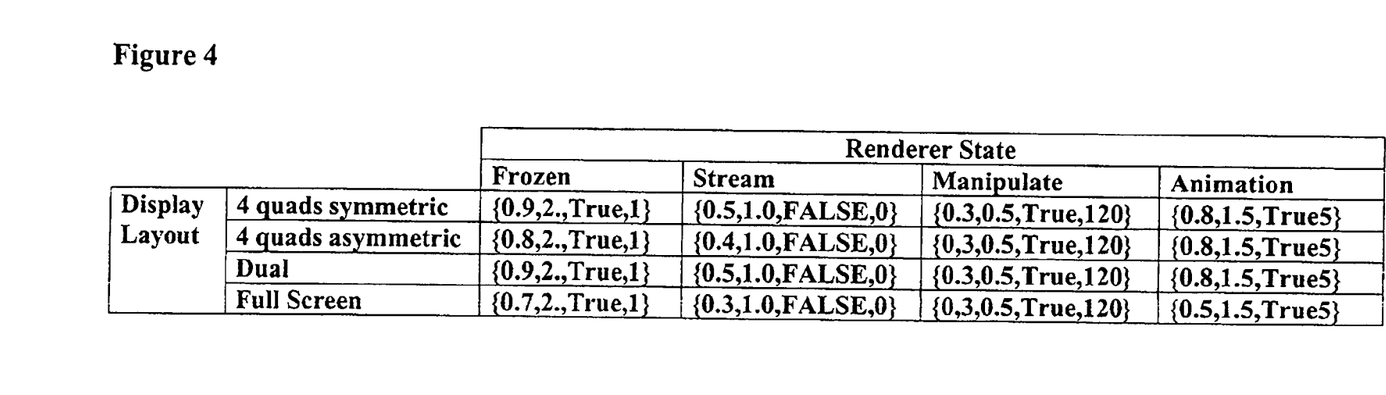
FIG. 4 is a chart example embodiment of rendering parameter values for four different states.

Based on the selected state and any display layout, the rendering parameters are automatically selected. For example, the values for the parameters for each of the different states are stored in a memory structure. The values are then obtained from the memory for implementing the rendering. FIG. 4 shows one example table of settings where the values in brackets correspond to in-plane sampling factor, viewing direction sampling factor, Boolean interpolation flag and an interpolation threshold in a 256 value scale. Other values may be used. The values are selected based on the computation power, size of the display windows and other system or user considerations.

Additional inputs may control the sets selected for any given state. For example, B-mode versus Power Doppler mode imaging results in different settings. Since B-mode data is associated with a high quality, the Boolean flag for adaptive optimization through interpolation may be set to disable interpolation. Since power data has lesser resolution, interpolation is provided for power data in the same state. In one embodiment, adaptive interpolation is performed for B-mode data only in the manipulation state, but performed in power data in other states. By having different settings, different rendering quality is provided for different states.

Further versatility in quality and associated quality between states or within a same state is provided by setting an in-plane sampling density different than or as a separate variable than viewing direction sampling density. For example, the in-plane sampling density is a different value than the viewing direction sampling density. By changing the values independently of each other or as separate variables, a more optimum tradeoff of image quality and processing speed may be made as compared to having a common sampling density along all three dimensions.

By setting a Boolean flag for interpolation, a threshold for interpolation or combinations thereof for each of the different rendering states, additional quality settings and versatility are provided. The Boolean flag indicates whether any interpolation is to occur in a particular state. The threshold value indicates when possible interpolation is to be performed, such as thresholding a difference between adjacent data. Interpolation may decrease quality, but increase processing speed.

In act 42, one of the different rendering states is selected. For example, a user selects one of the rendering states. The user may configure an imaging system for real time streaming state operation. During the streaming state, the user may manipulate or change a rendering parameter, transitioning into the manipulation state. The user may alternatively or additionally freeze an image on the display, transitioning into the frozen state. For transition to the manipulation state, the quality of one or more images may decrease. Once the manipulation is complete, the quality may increase due to transition back to a streaming or frozen state. By transitioning from a streaming state to a frozen state, more processing time or power is provided for increasing quality. Similarly, transitioning from a frozen state to a streaming or manipulation state may reduce quality. Likewise, an animation state may transition to or from any of the various other states. In another embodiment, a transition between states occurs as a function of time or automatically. For example, at the end of available data set for a streaming state operation, the last image is displayed in a frozen state. As another example, after manipulation in the manipulation state, a transition to a frozen state or a streaming state will occur after a certain amount of time. While the user is using a system to perform three- or four-dimensional imaging, the rendering software automatically adjusts the image quality and associated parameters for rendering based on the state and the display layout.

The switch between the states is shown by the feedback arrow from the renderer 46 to the selection of states 42. Adjustment between the different quality settings is automatically performed in response to selection of a different rendering state. Due to the switch in state, a rendering quality parameter or a plurality of rendering quality parameters are altered in act 44. The alteration increases or decreases quality, such as the alteration increasing a quality for switching to the frozen state relative to ultrasound images in a streaming state. Rendering is then performed based on the settings for the currently selected state, such as rendering a statically displayed ultrasound image in a frozen state based on an alteration of settings from a streaming state to the frozen state.

In act 46, a three-dimensional representation of the volume is rendered in one of the different rendering states. For example, ultrasound images of a sequence are rendered in the streaming state as a function of in-plane sampling density, viewing direction sampling density, interpolation density, Boolean flag for interpolation, interpolation threshold or combinations thereof. The rendering is performed in response to user input, such as the user configuring the system for three-dimensional viewing. Other user input may include the switching between states.

Figure 6:
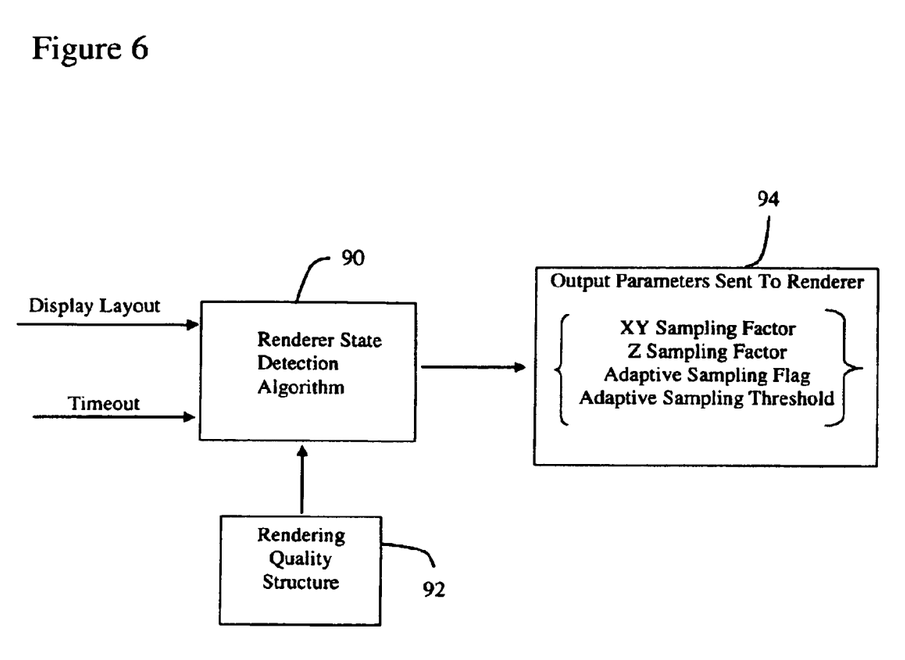
FIG. 6 is a flow chart diagram of one embodiment of software used for implementing the method of FIG. 3.

FIG. 6 represents the algorithm 90 for operating in different states. The timeout represents a duration based on which the renderer is considered to be or transitions to a frozen state. The rendering quality structure 92 is provided as a database, such as shown in FIG. 4. The timeout can be adaptively set by

We claim:

1. A method for adapting rendering quality for ultrasound imaging of a volume, the method comprising:
   (a) setting at least one ultrasound acquisition parameter value;
   (b) scanning the volume as a function of the at least one ultrasound acquisition parameter value, data resulting from the scanning having an acquisition quality;
   (c) setting with a processor at least one rendering quality parameter value of a rendering algorithm, wherein the setting with the processor of the at least one rendering quality parameter values is operable to determine a trade off between rendering algorithm speed and the rendering quality, wherein the setting with the processor of the at least one rendering quality parameter value is a function of the at least one ultrasound acquisition parameter value, wherein the rendering quality is different from the acquisition quality, and wherein the setting with the processor matches rendering performance to the acquisition quality;
   (d) rendering an ultrasound image from data acquired by the scan of (b), the rendering being a function of the at least one rendering quality parameter value; and
   (e) controlling (a) with a single quality control user input labeled for different quality levels, the single control user input operable to select the at least one ultrasound acquisition parameter value from a range of settings;
   wherein (c) is performed free of user input other than the single control user input of (e).

2. The method of claim 1 wherein (a) comprises setting the at least one ultrasound acquisition parameter value as a value for one of: an azimuthal beam spacing, an elevational beam spacing, a frame spacing, a depth, an imaging frequency, parallel beam processing and combinations thereof.

3. The method of claim 1 wherein (a) comprises setting the at least one ultrasound acquisition parameter value in response to user input.

4. The method of claim 1 wherein (e) comprises controlling with the single control user input, the labeling of the single control user input indicating a range of image qualities, the selected at least one ultrasound acquisition parameter value and set at least one rendering quality parameter value corresponding to an indicated image quality of the range of image qualities.

5. The method of claim 1 wherein (a) comprises setting at least four ultrasound acquisition parameter values as values for four of: an azimuthal beam spacing, an elevational beam spacing, a frame spacing, a depth, a 2D field-of-view, a 3D field-of-view, and/or an imaging frequency;
   wherein (b) comprises scanning as a function of the values.

6. The method of claim 1 wherein (c) comprises setting the at least one rendering quality parameter as a value for one of: in-plane sampling density, viewing direction sampling density, flag for the in-plane adaptive sampling, adaptive sampling threshold, an interpolation density and combinations thereof.

7. The method of claim 6 wherein (c) comprises setting values for in-plane sampling density and viewing direction sampling density as a function of the at least one ultrasound acquisition parameter value.

8. The method of claim 1 wherein (a) comprises setting an acquisition speed and wherein (c) comprises substantially matching a rendering speed to the acquisition speed.

9. The method of claim 1 wherein (c) comprises automatically setting the at least one rendering quality parameter value as a function of the at least one ultrasound acquisition parameter value.

10. The method of claim 1 wherein (b) and (d) are repetitively performed in a streaming state of operation, a sequence of ultrasound images being generated in the streaming state; further comprising:
   (e) switching to a frozen state of operation, a frozen ultrasound image statically displayed in the frozen state;
   (f) altering the at least one rendering quality parameter value, the alteration increasing a quality of the frozen image relative to the ultrasound images of the sequence.

11. A system for adapting rendering quality for ultrasound imaging of a volume, the system comprising:
   one or both of a beamformer system and a controller operable to scan or to cause the scan of the volume as a function of at least one ultrasound acquisition parameter value as a value selected for one of: an azimuthal beam spacing, an elevational beam spacing, a frame spacing, a 2D field-of-view, a 3D field-of-view, an imaging frequency, parallel beam processing and combinations thereof; and
   a three-dimensional rendering processor operable to render an ultrasound image representing the volume from data acquired by the beamformer as a function of the at least one ultrasound acquisition parameter value, the rendering being a function of at least one rendering quality parameter value, the at least one rendering quality parameter value being set as a function of the at least one ultrasound acquisition parameter value, the at least one rendering quality parameter value set as a value for one of: in-plane sampling density, viewing direction sampling density, an interpolation density and combinations thereof such that a resolution of the rendered ultrasound image is set as a function of the acquisition parameter value.

12. The system of claim 11 wherein the beamformer system is operable to scan as a function of at least four ultrasound acquisition parameter values as values for at least four of: an azimuthal beam spacing, an elevational beam spacing, a frame spacing, and an imaging frequency;
   wherein the three-dimensional rendering processor is operable to set values for in-plane sampling density and viewing direction sampling density as a function of the at least four ultrasound acquisition parameter values.

13. The system of claim 11 further comprising:
   a user input connected with the beamformer system and the three-dimensional rendering processor, the user input operable for indicating a range of image qualities, the selected at least one ultrasound acquisition parameter value and the set least one rendering quality parameter value corresponding to an indicated image quality of the range of available qualities.

14. The system of claim 11 wherein the three-dimensional rendering processor is operable to automatically substantially match a rendering speed to an acquisition speed, the rendering speed responsive to the at least one rendering quality parameter value and the acquisition speed responsive to the at least one ultrasound acquisition parameter value.

* * * * *